United States Patent [19]

Fields

[11] Patent Number: 5,013,668
[45] Date of Patent: May 7, 1991

[54] METHOD OF ESTIMATING A CUMULATIVE EXPOSURE TO A COMPOUND OF A GAS AND APPARATUS THEREFOR

[75] Inventor: Bernard Fields, Middlesbrough, England

[73] Assignee: Imperial Chemical Industries PLC, London, England

[21] Appl. No.: 308,675

[22] Filed: Feb. 10, 1989

[30] Foreign Application Priority Data

Feb. 16, 1988 [GB] United Kingdom ................. 8803515

[51] Int. Cl.⁵ .......................................... G01N 21/00
[52] U.S. Cl. ................................... 436/168; 436/167; 436/807; 436/902; 422/61; 422/83; 422/86; 422/88; 435/807; 73/31.02; 73/31.03

[58] Field of Search ................. 436/91, 167, 168, 902, 436/807; 438/809; 422/61, 88, 103, 83, 86, 102, ; 73/23.34, 31.01, 31.02, 31.03; 435/807

[56] References Cited

U.S. PATENT DOCUMENTS

| | | | |
|---|---|---|---|
| 4,158,958 | 6/1979 | Braun | 73/23 |
| 4,258,000 | 3/1981 | Obermayer | 422/88 |
| 4,269,804 | 5/1981 | Kring | 422/61 |
| 4,790,857 | 12/1988 | Miksch | 422/61 |

Primary Examiner—David L. Lacey
Assistant Examiner—David Redding
Attorney, Agent, or Firm—Cushman, Darby & Cushman

[57] ABSTRACT

A method of estimating a cumulative exposure to a component of a gas which comprises contacting a liquid reagent held by surface tension in a reservoir with a body of the gas through a conduit into which substantially only diffusional migration of the component from the body of gas occurs.

8 Claims, 3 Drawing Sheets

METHOD OF ESTIMATING A CUMULATIVE EXPOSURE TO A COMPOUND OF A GAS AND APPARATUS THEREFOR

BACKGROUND OF THE INVENTION

1. Field of the Invention

This invention relates to a method of estimating a cumulative exposure to a component of a gas and apparatus therefor.

2. Description of the Related Art

It is frequently desirable to obtain an estimate of a cumulative exposure of people or things to a component of a body of gas to which they are exposed. For example this may be important where a component is potentially toxic and where a body of gas is to be breathed by human beings. It may also be desirable to establish such exposure of objects to a component of a body of gas in an enclosed space for example the level of oxygen in an inert atmosphere, or an insecticide in a greenhouse atmosphere.

Such estimates are commonly performed using apparatus which draws the gas through an absorbent using a pump. However pumps may be relatively expensive and if they do not pump at the intended rate due for example to an electrical fault or battery discharge or other fault, it can lead to a wrong estimate of the cumulative exposure. They may also be inconvenient for a worker to wear if the worker's personal exposure to the component is to be estimated during a period of work.

SUMMARY OF THE INVENTION

The present invention relates to a method of estimating a cumulative exposure to a component of a gas which comprises contacting a liquid reagent held by surface tension in a reservoir with a body of the gas through a conduit into which substantially only diffusional migration of the said component from the said body of gas occurs. The quantity of reagent charged to the reservoir is suitably 0.05 to 5 preferably 0.2 to 2 microliters.

If desired several conduits may be provided which may be in parallel. The conduit may be convoluted if desired but is suitably substantially linear. The culmulative exposure may be estimated by removal and analysis of the reagent or by observing a colour change in it. In the latter case the reservoir should comprise a translucent or preferably transparent zone so that the colour change may be observed without removal of the reagent from the reservoir. The colour change may be observed for example by looking down the conduit or if preferred by looking through a transparent wall of the reservoir.

It is known for example from the following papers; "A diffusive sampler for sub-parts-per-million levels of formaldehyde in air using chemosorption on 2,4-dinitrophenylhydrazine coated glass fibre filters", by J-O Levin, R Lindahl and K Anderson, and "The effects of air velocity on a liquid diffusive air sampler," by B-O Hallberg both being published in: "Diffusive Sampling—an alternative approach to workplace air monitoring," edited by A Berlin, R H Brown, and K J Saunders, published by Royal Society of Chemistry, London 1987 and "A new passive colorimetric air monitoring badge system of ammonia, sulfur dioxide and nitrogen dioxide" by Kring, E, Lautenberger, W, Baker, B, Douglas, G and Hoffmann, R, published in Am Ind Hyg Assoc J, 42, 373-381, 1981, to carry out diffusive sampling of gases using reagent liquids absorbed on filter paper or held behind gas permeable membranes which reagent liquids are subsequently analysed. In the former case it is necessary to wash the reagent off the filter paper before analysis and this produces inconveniently large volumes and reduces the sensitivity of subsequent analysis. In the latter case the use of a membrane increases the complexity of the devices. This also makes them less convenient to use and they may be prone to leakage.

When a colour change is to be used it is preferred that the method be simultaneously carried out with a number of reagents of differing sensitivity to the component. By this means the cumulative exposure may be visually estimated by observing which reagents have changed colour, the least sensitive reagent to have changed colour giving an indication of this. By "sensitivity" is meant the amount of the component which must be absorbed to produce the colour change. Alternatively the method may be simultaneously carried out using a number of samples of identical reagent to which differing diffusional access is available through their conduits, for example by using longer and/or narrower conduits to restrict access. In this case the colour change in the sample with most restricted access indicates the cumulative exposure.

In a further form of the invention the reagent is a solvent for a component of a gas. The quantity of gas dissolved may be estimated by analytical or physical means at the conclusion of the period of exposure. If necessary the reagent may be cooled to increase the solubility of a component of a gas in the reagent.

To minimise displacement of the reagent by shock the quantity of liquid reagent within the reservoir is preferably small so that surface tension effects will be sufficient to immobilise it during an impact, and/or the viscosity of the reagent may be increased by for example the addition of a viscosity increasing agent. Suitable viscosity increasing agents include high molecular weight derivatives of alkylene oxides for example ethylene oxide and or propylene oxide of which the molecules consist largely of residues of said alkylene oxides suitably of molecular weight of 1,000 to 100,000 and preferably 1,500 to 50,000, for example polyalkylene glycols. Suitable viscosity increasing agents are the materials sold by ICI C and P Limited under the trade name Emkarox HV165 or HV105.

The invention also comprises a sampling device for use in a method as aforesaid which comprises a conduit of ratio of equivalent internal diameter to length in the range 2:1 to 1:100 and preferably 1:1 to 1:10, removable means for closing one end of the conduit with a member containing a reservoir communicating with the conduit for holding the liquid reagent in a fixed and removable relationship with the conduit and means for closing the other end of the conduit with a gas permeable dust rejecting and gas motion limiting member. By equivalent internal diameter is meant the diameter of a circle of area equal to the internal cross sectional area of the conduit at right angles to its length. The invention further comprises a sampling device as aforesaid provided with cooling means for the reagent.

The invention also comprises a sampling device for use in a method as aforesaid which comprises at least two and preferably at least four readily visible reservoirs.

The sampling device may be filled with reagent immediately prior to use or supplied prefilled. Prefilled devices should be protected from atmospheric contamination prior to use by enclosure in an air-tight container. Individual devices may be protected from atmospheric contamination prior to use by for example an air-tight lid or removable gas impermeable strip isolating the reagent from the atmosphere. If the device is to accompany a moving workman to estimate his exposure to a body of gas, a pin or clip or other suitable attachment means may be provided for attachment of the device to his clothing.

The device may be worn inverted to minimise contamination from moisture or dust, in this way the device may be used without a gas permeable dust rejecting and motion limiting member.

DETAILED DESCRIPTION OF THE PRESENTLY PREFERRED EXEMPLARY EMBODIMENT

Figure 1:
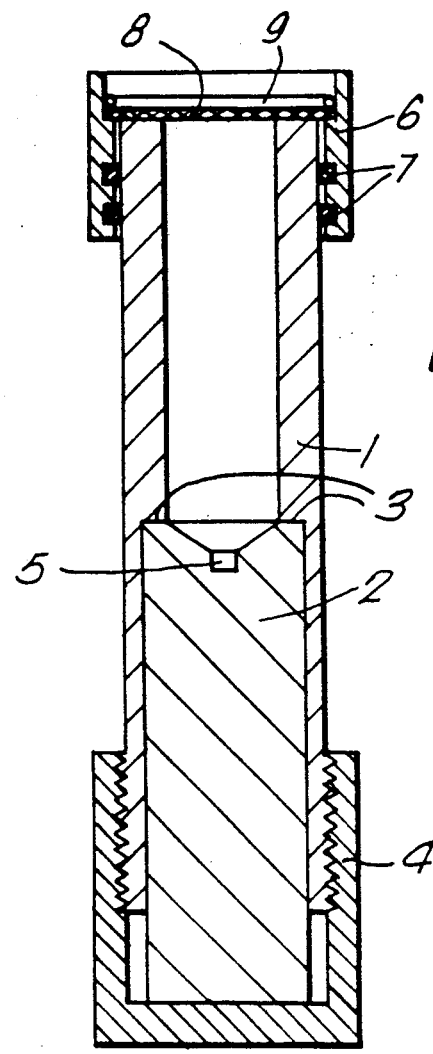
FIG. 1 is a schematic cross-sectional view of a device provided in accordance with the invention.

One form of the invention will now be described with reference to the accompanying FIG. 1 which shows a device in cross-section. This device comprises a conduit 1 and a member 2 releasably secured to a reproducible height against abutments 3 of the conduit by means of a screw cap 4 thereby closing one end of the conduit. At the end of member 2 facing the conduit is a reservoir 5. The gas space of the conduit is protected from contamination with solids such as dust by means of a filter cap 6 which releasably closes the opposite end of the conduit by means of a gas permeable filter 8 which is secured within the filter cap against an abutment by circlip 9. This filter may be a metal gauze which may be backed by an underlying membrane which may if desired by a water rejecting membrane. The filter cap is a push fit over the conduit and is held by 'O' rings 7.

In use the device is dismantled and a liquid reagent is placed within reservoir 5 by a syringe or similar means whereby the reagent is held in place by surface tension. The member 2 is inserted into conduit 2 and secured in a fixed position by tightening screw cap 4 until the member is brought to rest against the abutments 3 of the conduit. Filter cap 6 is pressed onto the top of the conduit.

The cumulative exposure of subjects for example the environment, people, machinery, plants and structures may be determined. The device may be used for monitoring atmospheric contamination by exposing it for a known period of time to the atmosphere to be tested. It may be used as a static testing device or may for example be secured to the clothing of a workman to give an indication of his cumulative exposure to a contaminant during a period of work.

Figure 2:
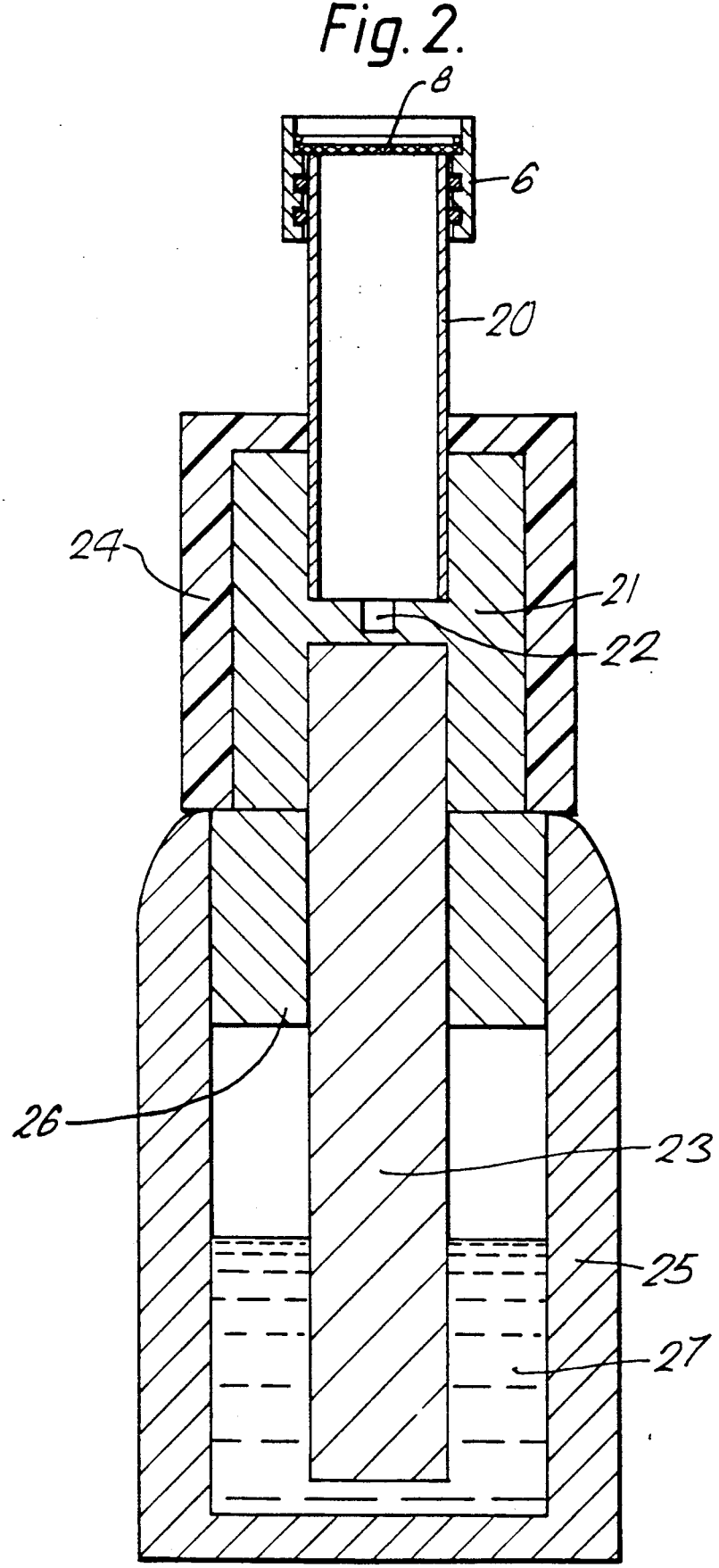
FIG. 2 is a schematic cross-section of an alternate configuration in accordance with the invention.

A second form of the invention is shown in cross-section in FIG. 2 which represents a sampling device as aforesaid provided with cooling means for the reagent. This device comprises a conduit 20 abutted within a cylindrical member 21, which is formed with coaxial bores at top and bottom the top bore leading to reservoir 22 which faces the conduit. The gas space of the conduit is protected from contamination with solids by means of a filter cap 6 as described in FIG. 1. Member 21 abuts one end of a copper rod 23 and is surrounded by insulation 24. The other end of the copper rod is surrounded by a Dewar vessel 25 which is fitted with a loose fitting plug 26.

In use the device is dismantled, a suitable reagent placed in reservoir 22 and a coolant 27 placed in Dewar vessel 25. The apparatus is reassembled as shown in FIG. 2. The reagent is cooled by conduction through copper rod 23 and exposed for a known period of time to the atmosphere to be tested. Gas permeable filter 8 typically contains a polymethyl silicone membrane which remains close to room temperature throughout the sampling procedure. When the period of time for exposure of the reagent to the atmosphere is complete, the reagent is removed by syringe and analysed by gas liquid chromatography. It is preferable to wash the reagent out of the reservoir with a solvent containing an internal standard and to withdraw part of the liquid with a syringe for such analysis for greater convenience and accuracy.

The device may be used for sampling gaseous components which do not react with the reagent and subsequent analysis thereof. Alternatively it may be used to sample the headspace gas from a liquid sample in order to extract and preconcentrate the component of interest.

Figure 3:
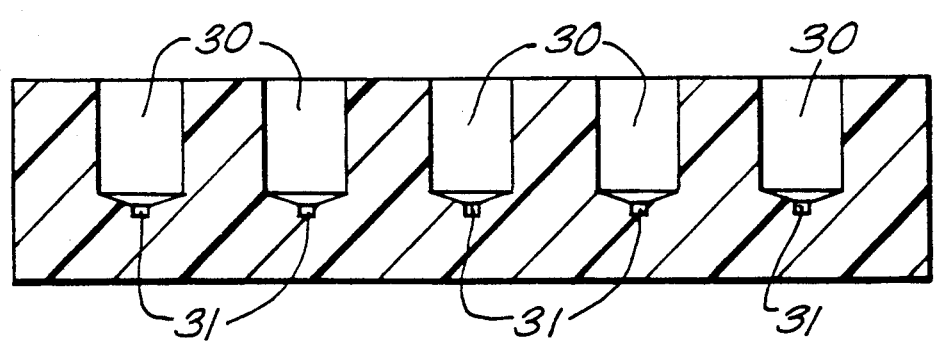
FIG. 3 is a schematic cross-sectional view of yet a further embodiment of the invention.

A third form of the invention is shown in cross section in FIG. 3 which represents a block of polytetrafluoroethylene formed with conduits 30 leading to reservoirs 31 in which are placed reagents of decreasing sensitivity to a component of the atmosphere and which change colour on absorption of increasing amounts thereof. The block may be worn by a workman who can estimate his cumulative exposure during the period when it is worn by observing which, if any, reagents have changed colour and can withdraw from a contaminated atmosphere when a safety limit is reached.

EXAMPLE 1

The following experimental data show the behaviour of a typical reagent and the linearity of its response to cumulative exposure in the invention.

A sampler as shown in FIG. 1 in which conduit 1 has an internal diameter 4.3 mm and abutments 3 are 15 mm from the open end of the pipe. The reservoir 5 has 1.1 mm internal diameter and is 1 mm deep, and the open end of the reservoir is about 17 mm from the open end of conduit 1. It was assembled with 1 ul of reagent in the reservoir. The reagent was 0.1M sulphuric acid in a mixture of water (20% by volume) in diethylene glycol (80% by volume).

The filter 8 was a metal gauze.

Figure 4:
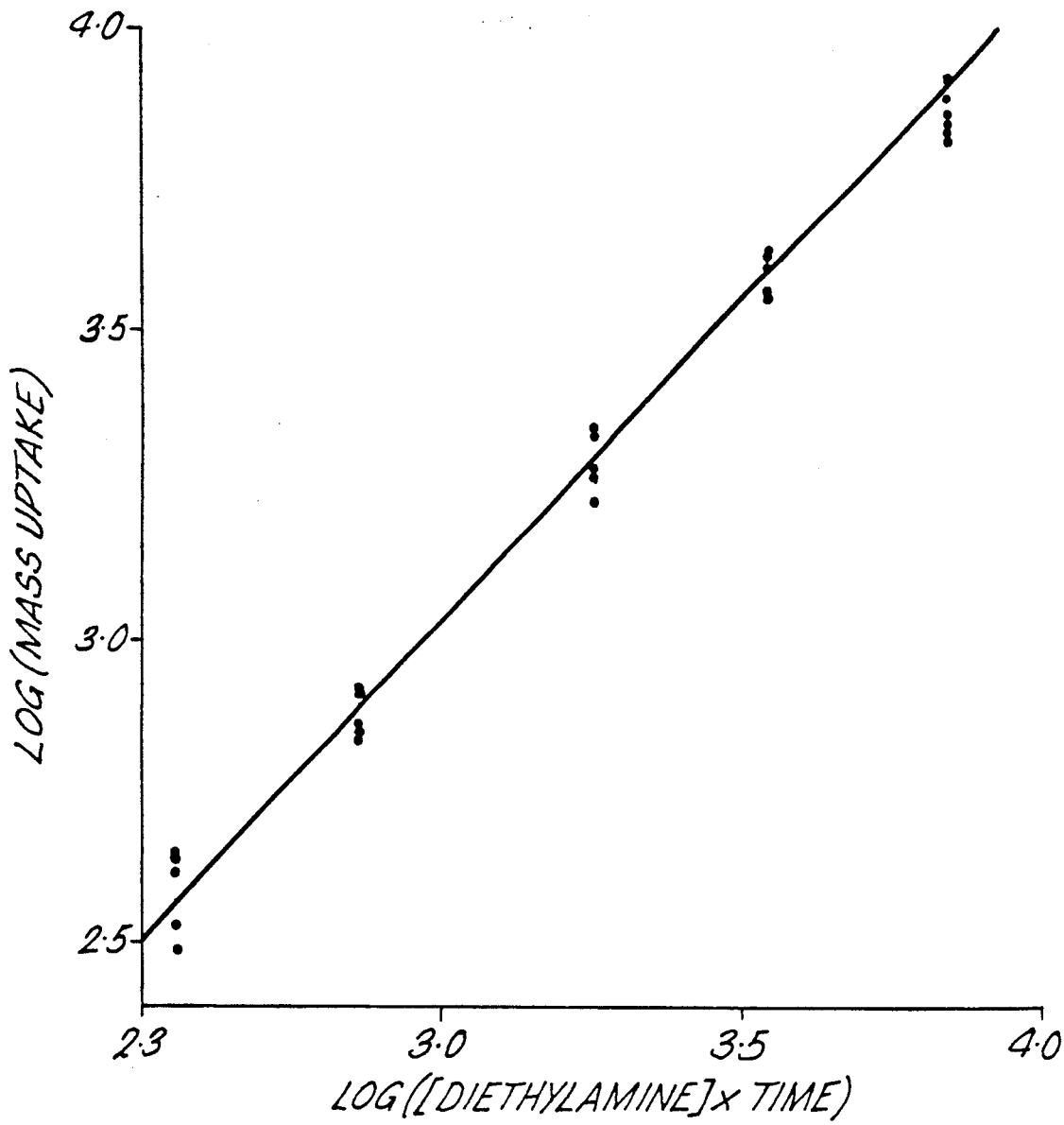
FIG. 4 is a graph which illustrates the measured mass of diethylamine gas absorbed by the device versus the concentration multiplied by the time of exposure of the device.

When six samplers prepared as above were exposed to five atmospheres of known diethylamine concentrations of 1.01, 2.06, 5.12, 10.2 and 20.4 parts per million (ppm) by volume for 6 hours and the mass of diethylamine absorbed M ng was measured and plotted against the concentration multiplied by the time of exposure (on $\log_{10}$ axes) a straight line graph was obtained (FIG. 4). Since the exposure time was constant the graph demonstrates that the mass uptake M is directly proportional to the concentration to which the sampler was exposed. The mass uptake rate U, calculated for each result was found to be constant within experimental error. U mean was 1.04 ng/ppm/min. The uptake rate U was also found to remain constant when exposure time was varied, when the diethylamine concentration was varied during exposure and when the velocity of air across the sampler face was varied. Thus when a sampler was prepared as above and exposed to an unknown concentration of diethylamine for 240 minutes and the sampler was found by internal standard gas chromatography to contain 1765 ng of diethylamine the average concentration to which the sampler had been exposed was calculated as 7.07 ppm diethylamine. At the end of each test the reagents were washed out mixed with excess alkaline solution and analysed by gas chromatography.

EXAMPLE 2

The procedure of example 1 was repeated except that a polymethyl silicone water rejecting membrane underlay the metal gauze of filter 8 and using 0.7 ul of 0.6M sulphuric acid in a mixture of water (7.5% by volume) in glycerol (92.5% by volume) was used, as reagent. The sampler was exposed to a number of amines simultaneously, each of known concentration of 5 ppm, for 310 minutes. The mass uptake rate 4, calculated for each amine was as follows:

| Amine | Uptake rate (U) ng/ppm/min |
|---|---|
| monomethylamine | 0.45 |
| dimethylamine | 0.69 |
| trimethylamine | 0.61 |
| monoethylamine | 0.65 |
| diethylamine | 0.93 |
| triethylamine | 1.47 |
| monoisopropylamine | 0.69 |
| diisopropylamine | 1.22 |

EXAMPLE 3

The procedure of example 1 was repeated using a filter 8 as described in example 2 and using 0.8 ul of a mixture of N-benzylethanolamine (5% by volume) in a polyalkylene glycol ether, molecular weight 2,000 sold commercially as "Emkarox" VG 217 W (95% by volume), as reagent. The sampler was exposed to a known concentration of 2 ppm formaldehyde in air for 4 hours. The mass of formaldehyde absorbed by reaction with N-benzylethanolamine to produce 3-benzyloxazolidine was measured and the mass uptake rate U, calculated for formaldehyde as 0.85 ng/ppm/min.

EXAMPLE 4

A sampler consisting of a translucent plastic tube internal diameter 4.4 mm of which one end is closed by a flat surface which accommodates a central recess 1.1 mm internal diameter 0.8 mm depth serving as a reservoir, the tube length from reservoir to its open end being 10 mm was used for the following tests.

A freshly prepared mixture of 0.4M sodium carbonate, diethylene glycol (67.5% by volume), "Emkarox" HV105 (12.5% by volume), methanol (5% by volume), thymol blue (250 mg/l) and water (15% by volume) (1 microliter) was placed in the reservoir. The sampler was exposed to 20 ppm hours of hydrochloric acid resulting in a colour change of reagent from green to yellow. On exposure to a further 20 ppm hours of hydrochloric acid the reagent changed colour from yellow to red.

EXAMPLE 5

A sampler as shown in FIG. 3 was then used in which the conduits were 4.5 mm diameter and 10 mm deep and the reservoirs were 1 mm diameter by 1 mm deep. The resevoirs were filled in order with 0.8 ul of reagents comprising 0.001, 0.002, 0.004, 0.010, 0.02, 0.05 and 0.1M hydrochloric acid and 0.004 g bromocresol green in 80%, diethylene glycol, 0.8% methanol (by volume) the balance being water.

The sampler was exposed for the periods stated in the Table below to the stated concentrations of diethylamine.

When the sampler has absorbed an amount of diethylamine almost equal in moles to the amount of hydrochloric acid in the sampler the solution turns from yellow to blue. The presence of a symbol B (blue), Y (yellow) or G (green) in a box in Table 1 indicates that the absorbing solution with the acid concentration given to the left has been exposed to the diethylamine concentration for the time given above.

There are two such symbols in each box. The symbol on the right is the actual colour indication noted after the exposure time. G (green) means that the colour is in the process of changing from yellow to blue. The symbol on the left is the colour of the solution which would be expected given the uptake rate of 1.71 ng/ppm/min for diethylamine which has been obtained experimentally. The relationship between exposure concentration and the colour changes of the solutions demonstrates that the device can be used for measuring average exposure concentrations. The good agreement between the calculated colour and actual colour after exposure demonstrates that the calculation procedures can be used to determine unknown concentrations using the procedure. Thus when given solutions of 0.002, 0.004, 0.010, 0.020 and 0.050M hydrochloric acid were exposed to an atmosphere and the first three soluions only turned blue the diethylamine concentration was calculated as $1.6 \pm 0.5$ ppm v/v when the actual atmosphere concentration was 1.6 ppm v/v (see column 8 of Table 1).

TABLE 1

| [H+] M | EXPOSURE TIME 166 MIN Diethylamine Concentration ppm | | | | | | | | | | EXPOSURE TIME 332 MIN Diethylamine concentration ppm | | | | | | | | | |
|---|---|---|---|---|---|---|---|---|---|---|---|---|---|---|---|---|---|---|---|---|
| | 0 | | 0.16 | | 1.6 | | 8.08 | | 20.2 | | 0 | | 0.16 | | 1.6 | | 8.08 | | 20.2 | |
| 0.001 | Y | Y | Y | G | | | | | | | Y | Y | B | B | | | | | | |
| 0.002 | Y | Y | Y | Y | B | B | B | B | | | Y | Y | Y | Y | B | B | B | B | | |
| 0.004 | Y | Y | Y | Y | B | B | B | B | B | B | Y | Y | Y | Y | B | B | B | B | B | B |
| 0.010 | | | | | Y | Y | B | B | B | B | | | | | B | B | B | B | B | B |
| 0.020 | | | | | Y | Y | B | G | B | B | | | | | Y | Y | B | B | B | B |
| 0.050 | | | | | Y | Y | B | G | B | G | | | | | Y | Y | B | B | B | B |

TABLE 1-continued

| [H+] | EXPOSURE TIME 166 MIN Diethylamine Concentration ppm | | | | | EXPOSURE TIME 332 MIN Diethylamine concentration ppm | | | | |
| --- | --- | --- | --- | --- | --- | --- | --- | --- | --- | --- |
| M | 0 | 0.16 | 1.6 | 8.08 | 20.2 | 0 | 0.16 | 1.6 | 8.08 | 20.2 |
| 0.100 | | | | Y | Y | | | | B | B |

Theoretical and actual colour indication after exposures.
Y = Yellow
G = Green - partly change colour
B = Blue
The first colour is the theoretical colour.

I claim:

1. A method of determining a cumulative exposure to a component of a gas, comprising:
   providing a reservoir means;
   providing conduit means for defining a path of communication between said reservoir means and a body of gas to be monitored, said conduit means allowing substantially only diffusional migration of a component of interest of the gas from the body of gas to the reservoir means;
   placing a liquid reagent in said reservoir means;
   holding said liquid reagent in said reservoir means substantially only by surface tension;
   exposing said liquid reagent to said body of gas through said conduit means
   and determining the amount of the component of gas absorbed by the liquid reagent.

2. A method as in claim 1, wherein said step of placing a liquid reagent comprises placing a liquid reagent which is a color indicator.

3. A method as in claim 2, wherein said step of providing a reservoir means comprises providing a plurality of reservoirs and wherein said step of placing a liquid reagent comprises placing liquid reagents of differing sensitivity to the component of interest to be measured in each said reservoir.

4. A method as in claim 2, wherein said step of providing a reservoir means comprises providing a plurality of reservoirs and wherein said step of providing a conduit means comprises providing conduits having differing diffusional access between said reservoirs and the body of gas.

5. A method as in claim 1, wherein said step of placing a liquid reagent comprises placing a liquid reagent which is a solvent for the component of interest.

6. A method as claimed in claim 1, wherein said step of placing a liquid reagent comprises placing a reagent comprising a viscosity increasing agent.

7. A method as claimed in claim 1, wherein said step of providing a conduit means comprises providing a conduit having a downwardly opening inlet for minimizing ingress of dust into said reservoir means.

8. A method as in claim 1, wherein said body of gas and said liquid reagent are in substantially unimpeded gas contact through the conduit means.

* * * * *